US007777731B2

(12) United States Patent  
Baumgart (10) Patent No.: US 7,777,731 B2
(45) Date of Patent: Aug. 17, 2010

(54) SYSTEM AND METHOD FOR SELECTION OF POINTS OF INTEREST DURING QUANTITATIVE ANALYSIS USING A TOUCH SCREEN DISPLAY

(75) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 733 days.

(21) Appl. No.: 11/610,640

(22) Filed: Dec. 14, 2006

(65) Prior Publication Data

US 2008/0139895 A1 Jun. 12, 2008

Related U.S. Application Data

(60) Provisional application No. 60/829,326, filed on Oct. 13, 2006.

(51) Int. Cl.
    G09G 5/00 (2006.01)
(52) U.S. Cl. ......................................... 345/173; 345/1.1
(58) Field of Classification Search ........... 345/1.1–1.3, 345/173
    See application file for complete search history.

(56) References Cited

U.S. PATENT DOCUMENTS

| 5,077,769 | A  | * | 12/1991 | Franciose .................. 378/98.2 |
| 6,670,950 | B1 | * | 12/2003 | Chin et al. .................. 345/173 |
| 7,106,479 | B2 | * | 9/2006  | Roy et al. .................. 358/3.27 |
| 7,556,602 | B2 | * | 7/2009  | Wang et al. .................. 600/437 |
| 2002/0137014 | A1 | * | 9/2002 | Anderson et al. ........... 434/262 |
| 2002/0168618 | A1 | * | 11/2002 | Anderson et al. ........... 434/262 |
| 2002/0190920 | A1 | * | 12/2002 | Kung .......................... 345/3.1 |
| 2003/0025678 | A1 | * | 2/2003 | Lee et al. .................... 345/173 |
| 2004/0076262 | A1 | * | 4/2004 | Shao et al. .................. 378/196 |
| 2004/0252074 | A1 | * | 12/2004 | Schaper ...................... 345/1.1 |
| 2005/0040999 | A1 | * | 2/2005 | Numano ...................... 345/1.1 |
| 2005/0245817 | A1 | * | 11/2005 | Clayton et al. .............. 600/424 |
| 2006/0055625 | A1 | * | 3/2006 | Vaccarelli ................... 345/1.1 |
| 2006/0098090 | A1 | * | 5/2006 | Bernard et al. ................ 348/77 |
| 2006/0262139 | A1 | * | 11/2006 | Rahn .......................... 345/629 |
| 2008/0158335 | A1 | * | 7/2008 | Baumgart ................. 348/14.03 |

* cited by examiner

Primary Examiner—Amare Mengistu
Assistant Examiner—Dmitriy Bolotin (57) ABSTRACT

A system for selecting points of interest on an anatomical image includes a main image display; a touch-screen display; a processing unit; and a network configured to interface the processing unit with the main image display and with the touch-screen display. An image displayed on the main display is concurrently displayed on the touch-screen display. The touch-screen display and the main image display concurrently display anatomical points of interest and the touch-screen display is configured to enable selecting anatomical points of interest by touching the points of interest on the touch-screen display. Touching of the points of interest can be effected by a user touching the touch-screen display, by a stylus, by a light pen, by a mouse, by a track ball, and by a joystick control. A corresponding method is also disclosed. Quantitative results are displayed on the main display.

12 Claims, 5 Drawing Sheets

SYSTEM AND METHOD FOR SELECTION OF POINTS OF INTEREST DURING QUANTITATIVE ANALYSIS USING A TOUCH SCREEN DISPLAY

CROSS-REFERENCE TO RELATED APPLICATIONS

This application claims priority under 35 U.S.C. §119 to U.S. Provisional Patent Application Ser. No. 60/829,326 filed on Oct. 13, 2006 entitled "Touch-Screen Selection of Points of Interest During Quantitative Analysis", the entire contents of which are incorporated by reference herein. This application cross-references concurrently filed U.S. patent application Ser. No. 11/610,591 by John Baumgart, entitled "System and Method for Selection of Anatomical Images for Display Using a Touch-Screen Display", the entire contents of which is incorporated by reference herein, and concurrently filed U.S. patent application Ser. No. 11/610,658 by John Baumgart, entitled "System and Method for Graphical Annotation of Anatomical Images Using a Touch-Screen Display", the entire contents of which is incorporated by reference herein.

BACKGROUND

1. Technical Field

The present disclosure relates to medical imaging systems.

2. Discussion of Related Art

Quantitative analysis of cardiac or vascular images typically requires input from the user to select anatomy of interest. Selection of an object by positioning a cursor at bedside using a joystick is cumbersome and slow. A mouse interface is unavailable at bedside to make this selection quicker. More particularly, the workflow is currently such that the user select points on images displayed on which may be, for example, coronary arteries. The selection is done in the examination room with the joystick of a touch-screen panel.

Quantitative analysis of specific vessels is performed. The quantitative analysis is focused on vessels such as coronary arteries that have narrowing as seen in x-rays, or function of the left ventricle of the heart. The user interface for these functions when carried out at patient bedside involves selecting an image for analysis, marking an area of a vessel to be analyzed by placing points with the joystick, and then having the software measure the vessel, find the narrowest point, and do other analysis. For analysis of the left ventricle, the user needs to select points on two images, one corresponding to the maximum expansion of the left ventricle, and one to the maximum contraction, after which the software analyzes the motion of the heart wall and efficiency of the left ventricle. The workflow and results of the quantitative analysis calculate indicators such as percent stenosis (narrowing) of arteries, and the efficiency and utility of the heart.

As can be appreciated from the foregoing, the user must select anatomical points of interest using either a mouse or joystick. At bedside, the user positions a cursor using the joystick, followed by selecting the image using a button, which is slow and awkward.

SUMMARY

The present disclosure relates to a simultaneous display and selection on a touch-screen display of points of interest on anatomical images during quantitative analysis that are displayed on a main panel display of an imaging system.

More particularly, the present disclosure relates to a system for selecting points of interest on an anatomical image. The system includes: a main image display; a touch-screen display; a processing unit; and a network configured to interface the main image display with the processing unit and configured to interface the touch-screen display with the processing unit. The system is configured such that an image displayed on the main display is concurrently displayed on the touch-screen display via the processing unit interfacing the main image display with the touch-screen display through the network, and such that the touch-screen display and the main image display concurrently display anatomical points of interest and the touch-screen display is configured to enable selecting at least one anatomical point of interest by touching the at least one point of interest on the touch-screen display.

The touching of the at least one point of interest on the touch-screen display may be effected by one of a stylus; a light pen; a mouse; a track ball; a joystick control; and the touch-screen display being touched by a user. The system may be configured such that following selection of the at least one anatomical point of interest, the main display displays quantitative results of the at least one anatomical point of interest on the at least one image. The system may also be configured such that following selection of the at least one anatomical point of interest, the touch-screen display displays a display mode displayed prior to the display of the anatomical points of interest. The system may further include a patient bed wherein the touch-screen display is positioned in proximity to the patient bed.

The present disclosure relates also to a method for selecting points of interest on an anatomical image. The method includes the steps of: providing a main image display; and a touch-screen display; displaying concurrently an image displayed on the main display on the touch-screen display; displaying concurrently anatomical points of interest on the image; and selecting at least one anatomical point of interest by touching the at least one point of interest on the touch-screen display. The touching of the at least one point of interest on the touch-screen display may be effected by touching the touch-screen display via one of a stylus; a light pen: a mouse; a track ball; a joystick control, and touching by a user. Following selecting the at least one anatomical point of interest the method may include the steps of displaying quantitative results of the at least one anatomical point of interest on the at least one image on the main display and/or displaying on the touch-screen display a display mode displayed prior to the display of the anatomical points of interest.

The present disclosure relates also to a touch-screen display for selecting points of interest on an anatomical image. The touch-screen display configured to interface with a main image display; a processing unit; and a network configured to interface the main image display with the processing unit and configured to interface the touch-screen display with the processing unit. The touch-screen display is configured such that an image displayed on the main display is concurrently displayed on the touch-screen display via the processing unit interfacing the main image display with the touch-screen display through the network, and such that the touch-screen display and the main image display concurrently display anatomical points of interest and the touch-screen display is configured to enable selecting at least one anatomical point of interest by touching the at least one anatomical point of interest on the touch-screen display.

The touching of the at least one point of interest on the touch-screen display may be effected by one of a stylus; a light pen; a mouse; a track ball; a joystick control; and the touch-screen display being touched by a user. The touch-screen display may be configured such that following selection of the at least one anatomical point of interest, the main display displays quantitative results of the at least one anatomical point of interest on the at least one image. The touch-screen display may also be configured such that following selection of the at least one anatomical point of interest, the touch-screen display displays a display mode displayed prior to the display of the anatomical points of interest.

The present disclosure relates also to a mouse configured to interface concurrently with a main display and a touch-screen display via a processing unit and via a network configured to interface the main image display with the processing unit and configured to interface the touch-screen display with the processing unit.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF EXEMPLARY EMBODIMENTS

Exemplary embodiments of the present disclosure will now be described in detail with reference to the figures, in which like reference numerals identify corresponding elements throughout the several views.

Referring to FIGS. 1-5, there is illustrated an exemplary angiographic x-ray system 10 as disposed in a patient examination room. A patient P is positioned on an examination bed 16. The x-ray or radiographic system 10 includes an image detector 40 supported by a support structure 12 and positioned over the examination bed 16. The image detector 40 is positioned over the patient P and over the examination bed 16 to detect the x-rays emitted from an x-ray source (not shown) under the bed 16 that enable recording the anatomical images. The radiographic system 10 includes a bank of main panel displays 20, e.g., overhead panel 22 and individual panel displays, e.g. panel displays 22A, 22B, 22C, 22C, 22D, 22E and 22F. The patient P and the main panel or image displays 20 are within view of a user U, e.g., a physician, seated at a control console 30. The main panel displays 20 are disposed on a distal side 16a of the examination bed 16 with respect to the user U.

Figure 1:
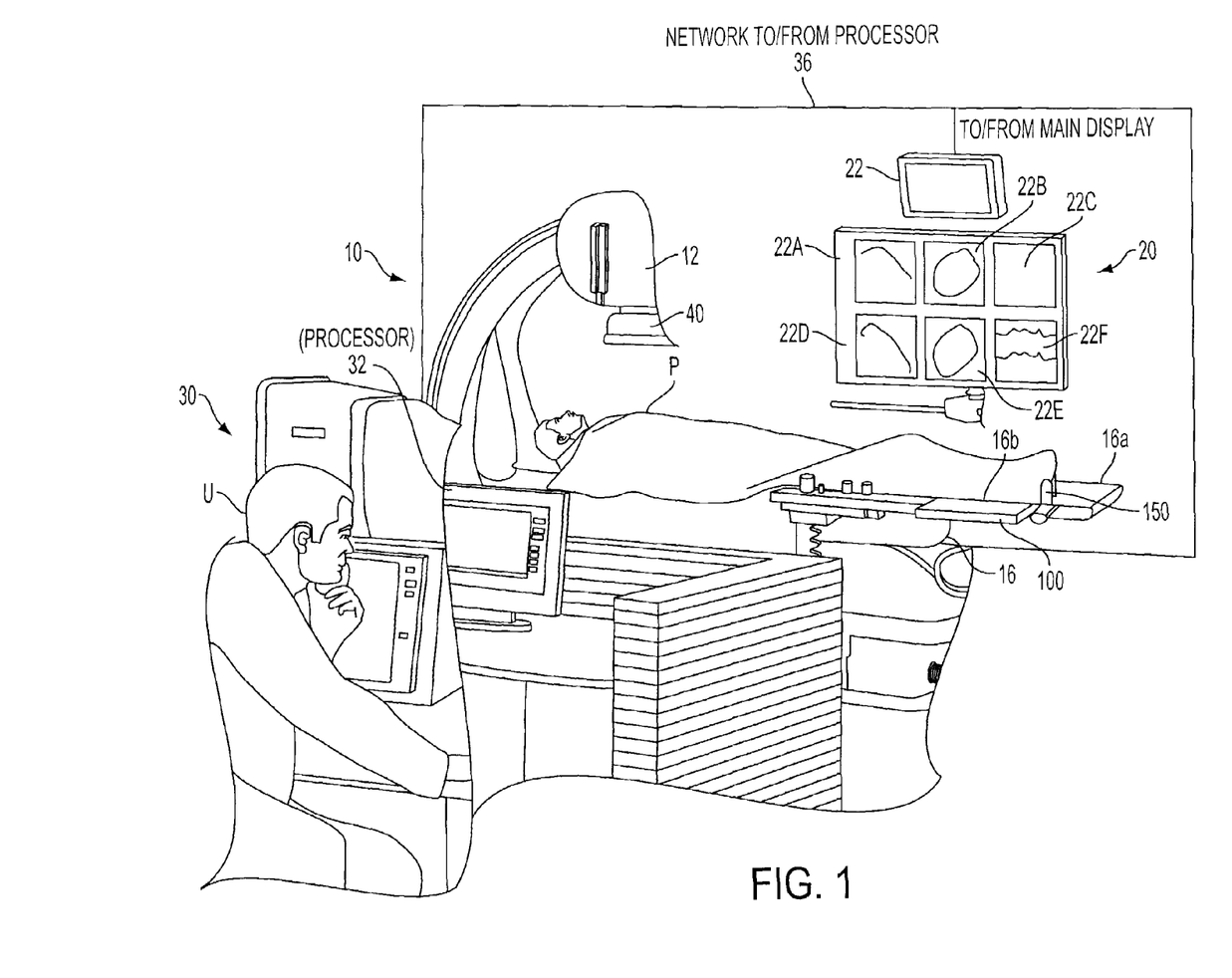
FIG. 1 is an overview of an exemplary angiographic X-ray system in a patient examination room illustrating a system user, a patient lying on a bed, main X-ray displays and a touch-screen display at the bedside.
Figure 2:
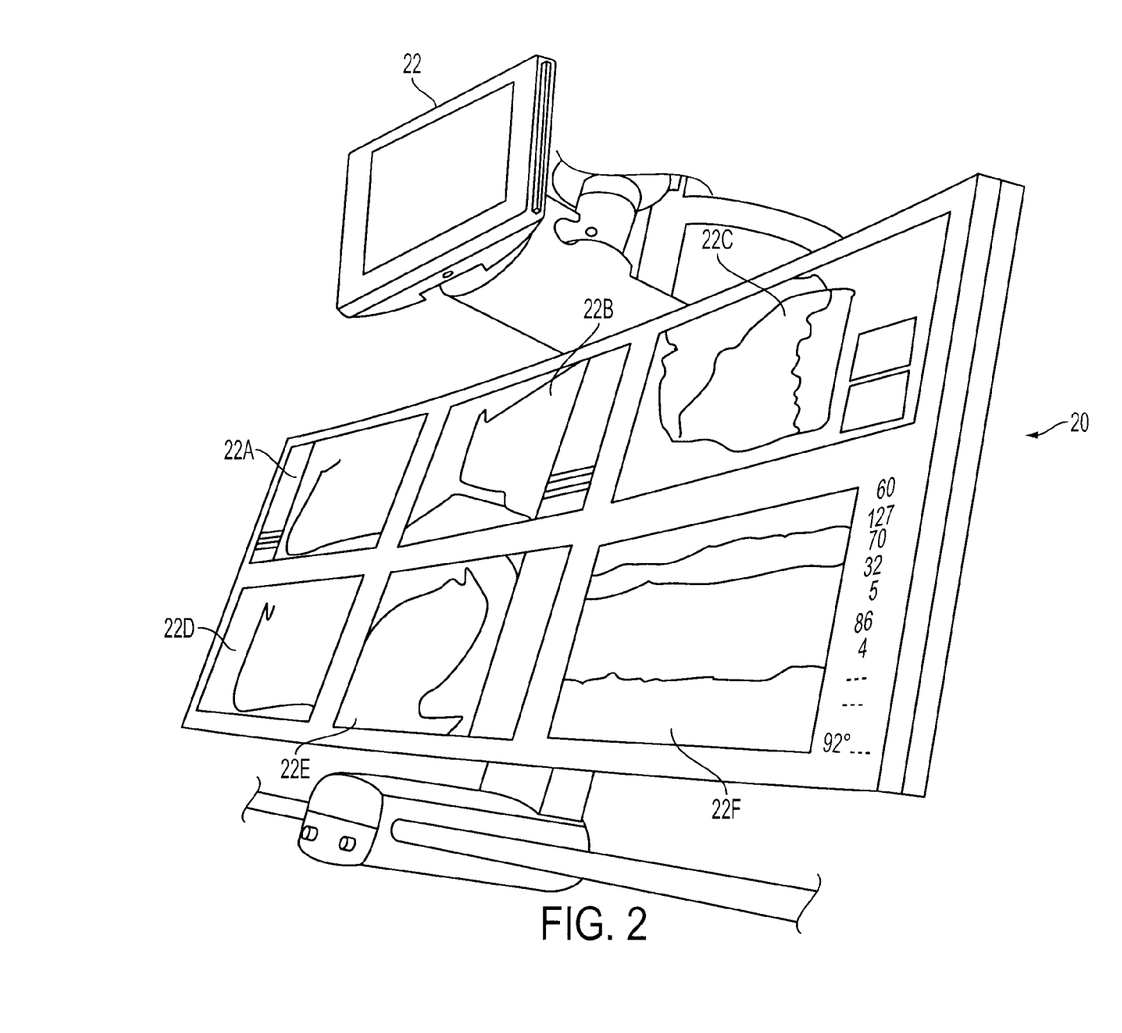
FIG. 2 is a perspective view of the main panel displays.
Figure 3:
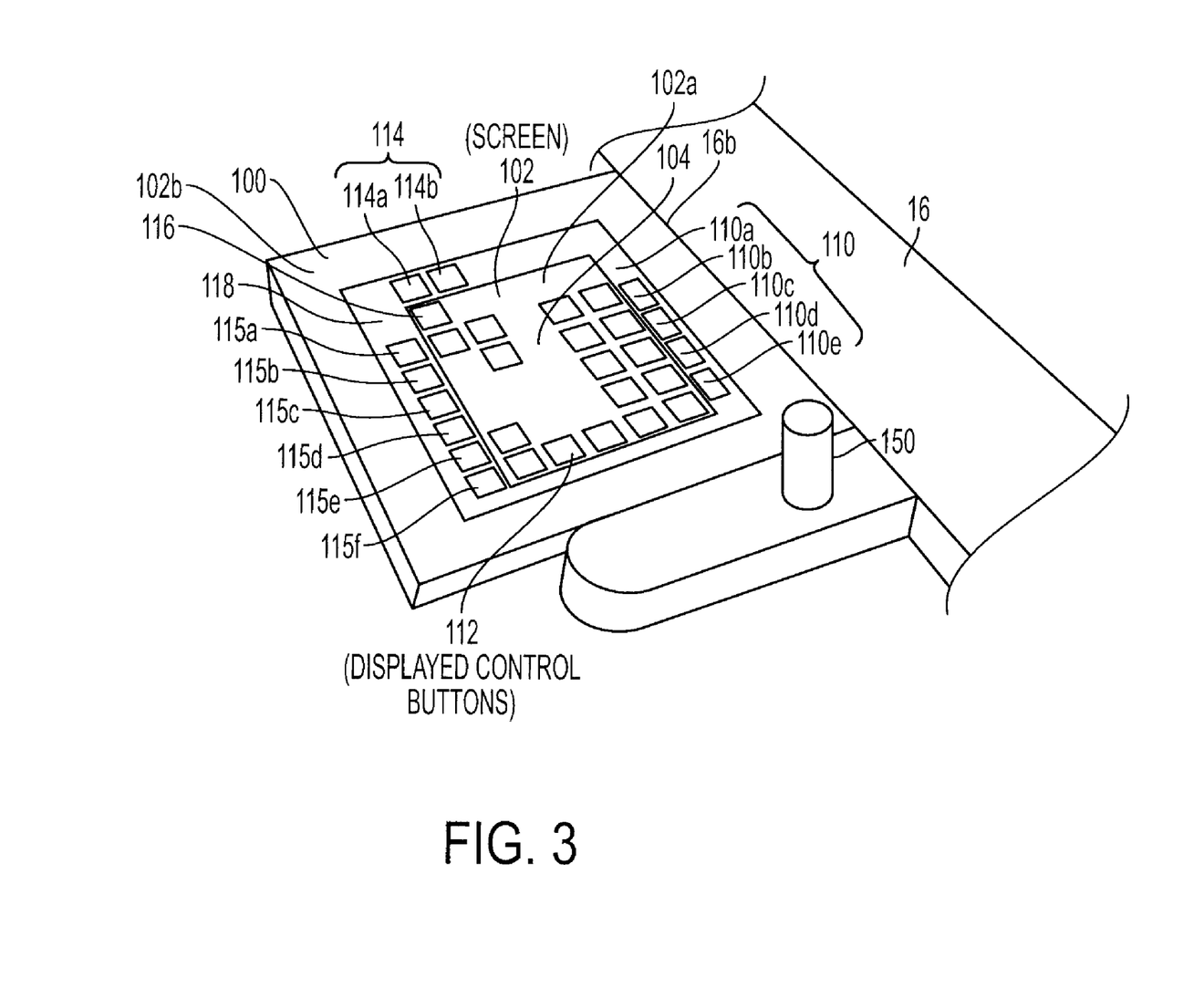
FIG. 3 is a perspective view of a touch-screen display according to the present disclosure before or after an image selection process.

As best illustrated in FIG. 3, the bed 16 includes a touch-screen display 100 according to the present disclosure with a joystick control 150, each disposed on a proximal side 16b of the examination bed 16. The touch-screen display 100 includes a touch-screen 102 that is sensitive to touch. The screen 102 may be subdivided into a main portion 102a and a border portion 102b around the main portion 102a. The user U may be standing at the proximal side 16b of the bed 16, where the touch-screen display 100 is located, and from which location the main panel or image displays 20 are also within view of the user U.

The radiographic system 10 further includes a processing unit 32 that may be located at the control console 30 and a network 36 that is configured to interface the main image display 20 with the processing unit 32 and is also configured to interface the touch-screen display 100 with the processing unit 32.

In one embodiment, an upper edge of the border portion 102b of the screen 102 includes a strip 110 of touch buttons or tabs, e.g., touch buttons 110a, 110b, 110c, 110d, and 110e, that is disposed proximate to the proximal edge 16b of the bed 16. The border portion 102b further includes a strip 114 of touch buttons or tabs, e.g., touch buttons 114a and 114b disposed on the left side of the border portion 102b and a strip 115 of touch buttons 115a, 115b, 115c, 115d, 115e and 115f disposed on the bottom side of the border portion 102b.

When one of the touch buttons, e.g., touch button 110b, is pressed on the screen 102, a particular series 112 of control buttons is displayed on the main portion 102a of the screen 102, as shown. If another touch button, e.g., touch button 110d is touched, a different series of control buttons (not shown) is displayed on the main portion 102a of the screen 102. However, the configuration, function, and position of touch buttons 114 on the border portion 102b does not change by touching the buttons 110a through 110e. In addition to the strips 110 and 114 of touch buttons, the screen 102 of the touch-screen display 100 further includes a "back", "cancel", or "return" button 116 that may be disposed in the border region 102b. The function of the "back", "cancel", or "return" button 116 is discussed in more detail below. Similarly, the screen 102 further includes an "Enter Selected Points of Interest" button 118. The function of the button 118 is also discussed in more detail below.

Figure 4A:
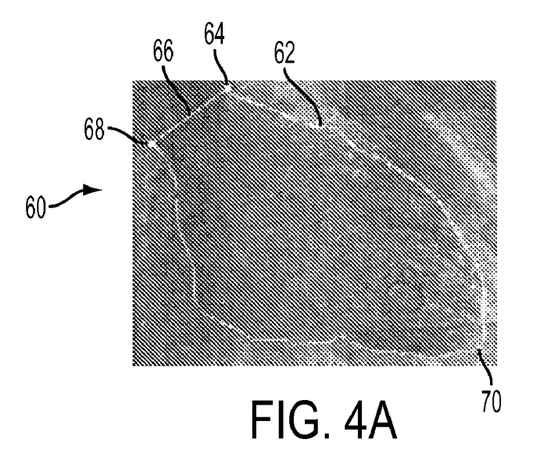
FIG. 4A illustrates an exemplary image of quantitative ventricular analysis as performed for an anatomical image, as exemplified by the left ventricle as defined by user-selected points marking the edges of the aortic valve and the apex of the left ventricle.

FIG. 4A illustrates an exemplary image 60 of quantitative ventricular analysis as exemplified by the left ventricle wherein user-selected points are defined to mark the edges of the aortic valve and the apex of the left ventricle. More particularly, the quantitative ventricular analysis is performed between points 64 and 68 on the edge of the aortic valve 62 defining a line 66 and an apex 70 of the aortic valve 62, with the points 64 and 68 and the apex 70 thereby defining a plane of the aortic valve 62.

Figure 4B:
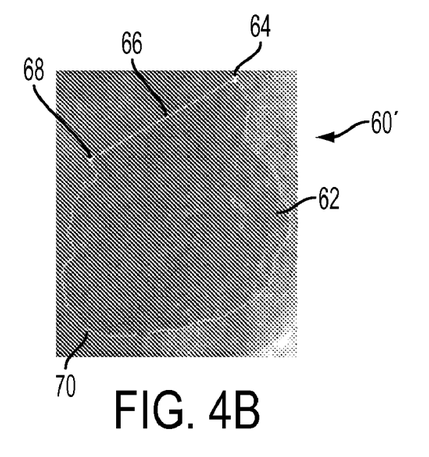
FIG. 4B illustrates an exemplary image of the quantitative ventricular analysis as performed for the anatomical image, as exemplified by the left ventricle as defined by the user-selected points marking the edges of the aortic valve and the apex of the left ventricle as illustrated in FIG. 4A, as viewed from a different x-ray projection.

FIG. 4B illustrates an exemplary image 60' of the quantitative ventricular analysis as exemplified by the left ventricle wherein the user-selected points marking the edges of the aortic valve and the apex of the left ventricle as illustrated in FIG. 4A, are viewed from a different x-ray projection of the aortic valve 62. Again, points 64 and 68 on the edge of the aortic valve 62 define line 66 and apex 70 of the aortic valve 62, with the points 64 and 68 and the apex 70 thereby defining the plane of the aortic valve 62 from a different angle of projection.

Figure 5:
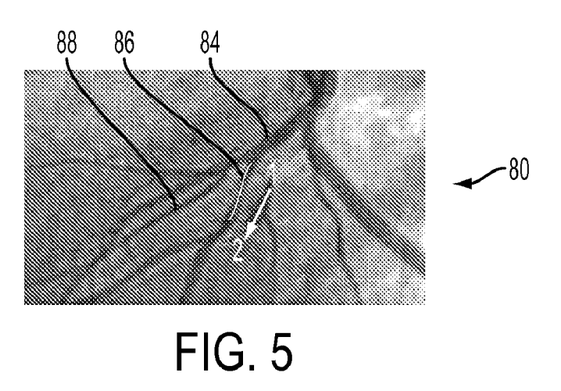
FIG. 5 illustrates an exemplary image of quantitative vascular analysis as performed on a blood vessel.

FIG. 5 illustrates an exemplary image 80 of quantitative vascular analysis as performed between points 84 and 88 defining a line 86 in a blood vessel 82.

In the prior art, the points 64 and 68, defining the line 66 (see FIGS. 4A and 4B), and the points 84 and 88, defining the line 86 (see FIG. 5), are displayed on the main image display 20 and selected either by clicking with a mouse that is provided at the control console 30 for the main displays 20 (see FIGS. 1 and 2) or by operating the joystick control 150 (see FIG. 3) of the touch-screen display 100.

Figure 6:
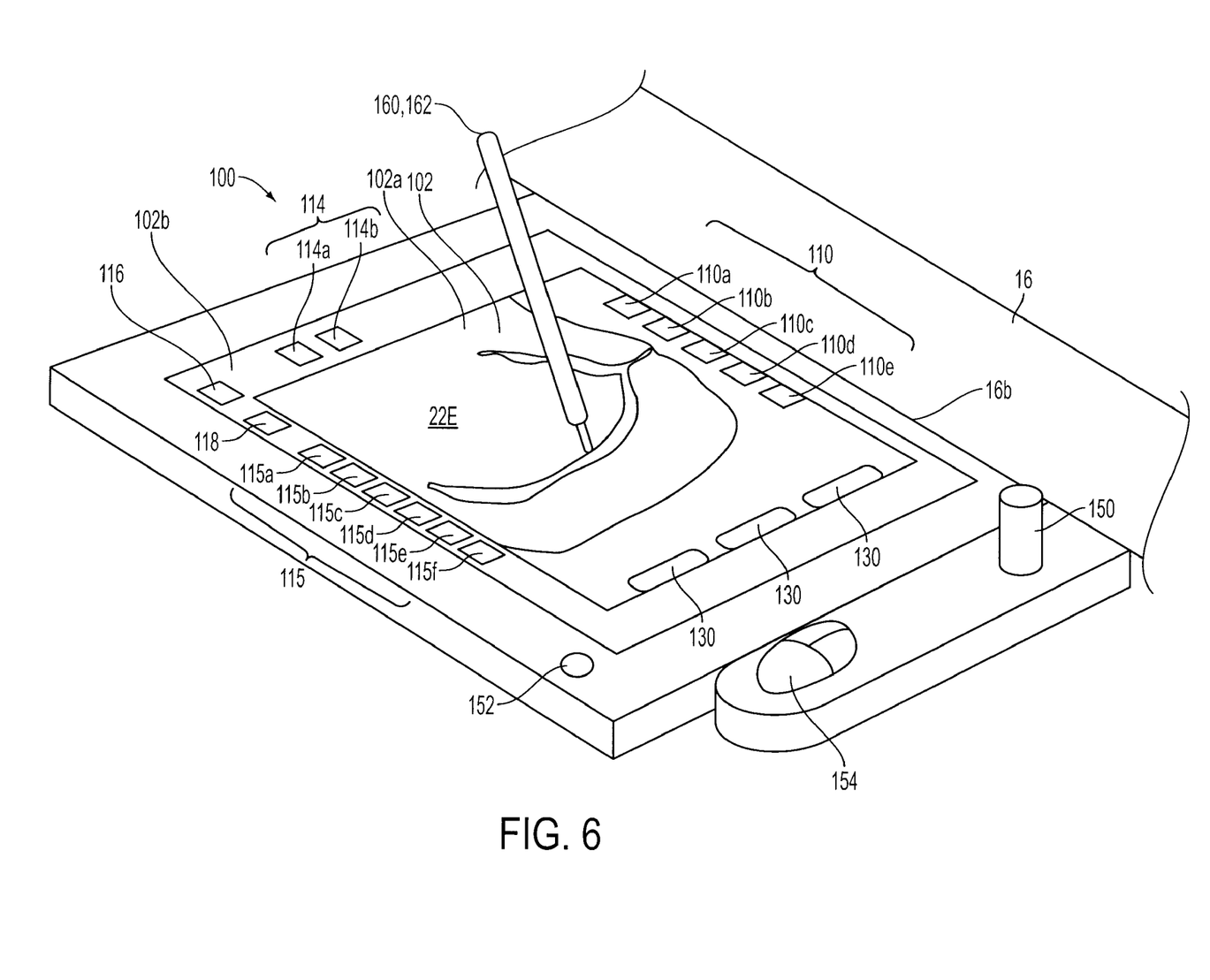
FIG. 6 is a perspective view of an exemplary image on the touch-screen display of FIG. 3 according to the present disclosure.

FIG. 6 illustrates exemplary image 22E (see FIGS. 1 and 2) displayed on the touch-screen display 100 according to the present disclosure. More particularly, upon the software requiring user input for selection of points of interest, e.g. points 64 and 68 (see FIGS. 4A and 4B), and points 84 and 88 (see FIG. 5), an image, e.g., image 22E that is currently displayed on the main display 20 (see FIGS. 1 and 2) is simultaneously displayed on the touch-screen display or console 100, positioned in proximity to the bed 16, e.g., on the side 16b thereof, as illustrated in FIG. 6, at which location the user U may stand. The touch-screen display 100 may include, in addition to the joystick 150, a track ball 152 and/or a mouse 154. The mouse 154 may be wired to the processor 32 or may be operatively coupled to the processor 32 wirelessly or contactlessly, e.g., via optical, electromagnetic, or acoustic waves. The mouse 154 may also be configured as a "built-in" touch panel and scroll design available for portable computers. The mouse 154 may be configured to interface concurrently with the main display 20 and the touch-screen display 100 via the processing unit 32 and the network 36 that is configured to interface the main image display 20 with the processing unit 32 and that is configured to interface the touch-screen display 100 with the processing unit 32. The embodiments are not limited in this context.

The touch-screen display 100 may also be operatively coupled to the processor 32 via a stylus 160 or light pen 162 (concurrently illustrated). The screen 102 may also display on at least one edge one or more thumbnails 130 that may be pressed for selection of the image, e.g., image 22E that is currently displayed on the main display 20 to be simultaneously displayed on the screen 102. The embodiments are not limited in this context.

Instead of being limited to selecting the points of interest only on the main display 20, the user U can now also select directly the points of interest, e.g., the points 64 and 68 and 70 (see FIGS. 4A and 4B), and points 84 and 88 (see FIG. 5), on the image 22E that is now displayed simultaneously on the touch-screen 102 of the touch-screen display 100. More particularly, the user U can use the stylus 160 or the light pen 162 to select directly on the touch-screen 102 the anatomical points of interest, thereby effecting touching of the touch-screen 102. The user U can also touch the screen 102 using a part of the user's body, e.g., one or more fingers, to select the points of interest. In addition, the user U can use the track ball 152 or the mouse 154 also to select directly on the touch-screen 102 the anatomical points of interest, thereby effecting the touching of the touch-screen 102. As defined herein, touching of the touch-screen 102 to select directly on the touch-screen 102 the anatomical points of interest may also be effected by the joystick control 150. Once the user U has definitively selected the anatomical points of interest, the user U can then press the "Enter Selected Points of Interest" button 118 on the touch-screen display 100 to enable the software to perform the quantitative analysis described above. Following selecting the at least one anatomical point of interest, the system 10 is configured such that the quantitative results of the at least one image, e.g., image 22E, are displayed on the main display 20. Also following selecting the at least one anatomical point of interest, a display mode displayed prior to the display of the anatomical points of interest, e.g., display mode 104 illustrated in FIG. 3, is displayed on the touch-screen display 100.

Although the anatomical image described herein is disclosed with respect to exemplary angiographic x-ray system 10, the embodiments of the present disclosure may be applied to other anatomical images and imaging systems such as, but not limited to, computer assisted tomography (CAT), magnetic resonance imaging (MRI), positron emission tomography (PET) and acoustic or sonogram images.

The present disclosure relates also to the touch-screen display 100 for selecting points of interest on an anatomical image, e.g., the points 64 and 68 and the apex 70 (see FIGS. 4A and 4B), and points 84 and 88 (see FIG. 5), displayed on the image 22E that is now displayed concurrently or simultaneously on the main image display 20. The touch-screen display 100, positioned in proximity to the bed 16, e.g., on side 16a thereof, is configured to interface with the main image display 20, the processing unit 32, and the network 36 that is configured to interface the main image display 20 with the processing unit 32 and configured to interface the touch-screen display 100 with the processing unit 32. The touch-screen display 100 is configured such that an image displayed on the main image display 20 is concurrently or simultaneously displayed on the touch-screen display 100 via the processing unit 32 interfacing the main image display 20 with the touch-screen display 100 through the network 36. The touch-screen display 100 is configured such that the touch-screen display 100 and the main image display 20 concurrently display anatomical points of interest, e.g., the points 64 and 68 and 70 (see FIGS. 4A and 4B), and points 84 and 88 (see FIG. 5) on the image 22E, and the touch-screen display 100 is configured to enable selecting at least one anatomical point of interest by touching the at least one anatomical point of interest on the screen 102 of the touch-screen display.

As described above, the touching of the at least one point of interest on the touch-screen display 100 may be effected by the stylus 160 or light pen 162, or by the mouse 154, the track ball 152, and the joystick control 150. The user U can also touch the touch screen 102 using a part of the user's body, e.g., one or more fingers, to select the points of interest. The touch-screen display 100 may be configured such that following selection of sufficient points for calculation of quantitative results for a given image, the main display 20 displays the quantitative results of that image. Also, the touch-screen display 100 may be configured such that following selection of the at least one anatomical point of interest, the touch-screen display 100 displays a display mode displayed prior to the display of the anatomical points of interest, e.g., display mode 104.

The present disclosure relates also to the mouse 154 that is configured to interface concurrently with the main display 20 and the touch-screen display 100 via the processing unit 32 and via the network 36 that is configured to interface the main image display 20 with the processing unit 32 and also configured to interface the touch-screen display 100 with the processing unit 32.

In addition, the present disclosure relates also to a method for selecting points of interest on an anatomical image, e.g., the points 64 and 68 and 70 (see FIGS. 4A and 4B), and points 84 and 88 (see FIG. 5) on the image 22E. The method includes the steps of providing the main image display 20 and the touch-screen display 100, displaying concurrently the image 22E displayed on the main display 20 on the touch-screen display 100, displaying concurrently anatomical points of interest on the image 22E, and selecting at least one anatomical point of interest, e.g., points 64 and 68 and 70, and points 84 and 88, by touching the at least one point of interest on the touch-screen display 100.

The method may be implemented such that the touching of the at least one point of interest on the touch-screen display 100 may be effected by touching the touch-screen display 100 via one of the stylus 160 or light pen 162; or by the mouse 154; the track ball 152; the joystick control 150; or touching by the user U, e.g., via a part of the body of the user U such as by one or more fingers. The method may be implemented such that following selecting the at least one anatomical point of interest, e.g., sufficient points for calculation of quantitative results for a given image, the method includes the step of displaying quantitative results of the at least one anatomical point of interest on the at least one image 22E on the main display 20. The method may also be implemented such that following selecting the at least one anatomical point of interest, the method includes the step of displaying on the touch-screen display 100 a display mode that was displayed prior to the display of the anatomical points of interest, e.g., display mode 104.

It will be understood that various modifications may be made to the embodiments disclosed herein. For example, although the above embodiments are described with reference to one particular configuration of the system, method and touch-screen display, the embodiments of the present disclosure may find application in conjunction with a system, method and touch-screen display having many different configurations. Accordingly, it is contemplated that the disclosure is not limited to such an application and may be applied to various embodiments.

What is claimed is:

1. A system for selecting points of interest on an anatomical image, the system comprising:
   a main image display;
   a touch-screen display presenting one or more user selectable thumbnail images of images presented in the main image display enabling a user to select an image displayed in the main image display for concurrent display on the touch-screen display;
   a processing unit; and
   a network configured to interface the main image display with the processing unit and configured to interface the touch-screen display with the processing unit,
   wherein the system is configured such that an image displayed on the main display is concurrently displayed on the touch-screen display via the processing unit interfacing the main image display with the touch-screen display through the network,
   wherein the system is configured such that the touch-screen display and the main image display concurrently display anatomical points of interest and the touch-screen display is configured to enable selecting at least one anatomical point of interest by touching the at least one point of interest on the touch-screen display, and wherein the system is configured such that in response to user selection of at least one anatomical point of interest for calculation of quantitative results for a given image, the main image display presents the quantitative results of that image in a first mode and the touch-screen display presents a display in a second mode previously presented prior to the display of the anatomical points of interest.

2. The system according to claim 1, wherein the touching of the at least one point of interest on the touch-screen display is effected by one of (a) a stylus; (b) a light pen: (c) a mouse; (d) a track ball; (e) a joystick control; and (f) the touch-screen display being touched by a user.

3. The system according to claim 1, wherein the system is configured such that following selection of the at least one anatomical point of interest, the main display displays quantitative results of the at least one anatomical point of interest on the at least one image.

4. The system according to claim 1, further comprising a patient bed wherein the touch-screen display is positioned in proximity to the patient bed.

5. A method for selecting points of interest on an anatomical image, the method comprising the steps of
   providing:
   a main image display; and
   a touch-screen display;
   displaying concurrently an image displayed on the main display on the touch-screen display;
   presenting one or more user selectable thumbnail images of images presented in the main image display enabling a user to select an image displayed in the main image display for concurrent display on the touch-screen display;
   displaying concurrently anatomical points of interest on the image;
   selecting at least one anatomical point of interest by touching the at least one point of interest on the touch-screen display; and
   in response to user selection of at least one anatomical point of interest for calculation of quantitative results for a given image, the main image display presents the quantitative results of that image in a first mode and the touch-screen display presents a display in a second mode previously presented prior to the display of the anatomical points of interest.

6. The method according to claim 5, wherein the touching of the at least one point of interest on the touch-screen display is effected by touching the touch-screen display via one of (a) a stylus; (b) a light pen: (c) a mouse; (d) a track ball; (e) a joystick control, and (f) touching by a user.

7. The method according to claim 5, further comprising the step of
   following selecting the at least one anatomical point of interest, displaying quantitative results of the at least one anatomical point of interest on the at least one image on the main display.

8. A touch-screen display system for selecting points of interest on an anatomical image, comprising
   a touch-screen display configured to interface with
   a main image display;
   a processing unit, said touch-screen display presenting one or more user selectable thumbnail images of images presented in the main image display enabling a user to select an image displayed in the main image display for concurrent display on the touch-screen display; and
   a network configured to interface the main image display with the processing unit and configured to interface the touch-screen display with the processing unit,
   wherein the touch-screen display is configured such that an image displayed on the main display is concurrently displayed on the touch-screen display via the processing unit interfacing the main image display with the touch-screen display through the network,
   wherein the touch-screen display is configured such that the touch-screen display and the main image display concurrently display anatomical points of interest and the touch-screen display is configured to enable selecting at least one anatomical point of interest by touching the at least one anatomical point of interest on the touch-screen display, and wherein the system is configured such that in response to user selection of at least one anatomical point of interest for calculation of quantitative results for a given image, the main image display presents the quantitative results of that image in a first mode and the touch-screen display presents a display in a second mode previously presented prior to the display of the anatomical points of interest.

9. The touch-screen display according to claim 8, wherein the touching of the at least one point of interest on the touch-screen display is effected by one of (a) a stylus; (b) a light pen: (c) a mouse; (d) a track ball; (e) a joystick control; and (f) the touch-screen display being touched by a user.

10. The touch-screen display according to claim 8, wherein the touch-screen display is configured such that following selection of the at least one anatomical point of interest, the main display displays quantitative results of the at least one anatomical point of interest on the at least one image.

11. The touch-screen display according to claim 8, wherein the touch-screen display is positioned in proximity to a patient bed.

12. A system for selecting points of interest on an anatomical image, the system comprising:

a main image display;

a touch-screen display presenting one or more user selectable thumbnail images of images presented in the main image display enabling a user to select an image displayed in the main image display for concurrent display on the touch-screen display;

a processing unit;

a network configured to interface the main image display with the processing unit and configured to interface the touch-screen display with the processing unit, wherein the system is configured such that an image displayed on the main display is concurrently displayed on the touch-screen display via the processing unit interfacing the main image display with the touch-screen display through the network, wherein the system is configured such that the touch-screen display and the main image display concurrently display anatomical points of interest and the touch-screen display is configured to enable selecting at least one anatomical point of interest by touching the at least one point of interest on the touch-screen display, wherein the system is configured such that in response to user selection of at least one anatomical point of interest for calculation of quantitative results for a given image, the main image display presents the quantitative results of that image in a first mode and the touch-screen display presents a display in a second mode previously presented prior to the display of the anatomical points of interest; and a mouse configured to interface concurrently with a main display and a touch-screen display via a processing unit and via a network configured to interface the main image display with the processing unit and configured to interface the touch-screen display with the processing unit.

* * * * *